(12) United States Patent
Moss

(10) Patent No.: US 9,301,903 B2
(45) Date of Patent: Apr. 5, 2016

(54) MULTI-LUMEN CATHETER

(71) Applicant: Gerald Moss, White Plains, NY (US)

(72) Inventor: Gerald Moss, White Plains, NY (US)

( * ) Notice: Subject to any disclaimer, the term of this patent is extended or adjusted under 35 U.S.C. 154(b) by 25 days.

(21) Appl. No.: 14/230,385

(22) Filed: Mar. 31, 2014

(65) Prior Publication Data

US 2015/0272831 A1   Oct. 1, 2015

(51) Int. Cl.
*A61M 3/00* (2006.01)
*A61J 15/00* (2006.01)
*A61L 29/04* (2006.01)
*A61L 29/14* (2006.01)
*A61M 5/00* (2006.01)
*A61M 25/00* (2006.01)

(52) U.S. Cl.
CPC .......... *A61J 15/0003* (2013.01); *A61J 15/0073* (2013.01); *A61L 29/041* (2013.01); *A61L 29/143* (2013.01); *A61M 5/007* (2013.01); *A61M 25/0026* (2013.01); *A61J 15/0049* (2013.01); *A61M 2025/0035* (2013.01)

(58) Field of Classification Search
CPC .............. A61J 15/0015; A61J 15/0026; A61J 2025/0035; A61J 2025/0036; A61J 25/0032
USPC .................................................. 604/910, 43
See application file for complete search history.

(56) References Cited

U.S. PATENT DOCUMENTS 5,556,390 A * 9/1996 Hicks ................ A61M 25/0023
                                                                    604/264
2011/0098660 A1* 4/2011 Porreca, Jr. ....... A61M 25/0026
                                                                    604/246

\* cited by examiner

*Primary Examiner* — Kevin C Sirmons
*Assistant Examiner* — Deanna K Hall
(74) *Attorney, Agent, or Firm* — Schmeiser, Olsen & Watts LLP

(57) ABSTRACT

A multi lumen gastrointestinal catheter is disclosed. The multi-lumen gastrointestinal catheter has a flexible partition separating a feeding and an aspiration channel. A third smaller inflation channel is positioned within the outside exterior wall at the site of the flexible partition to avoid kinking at the inflation channel site, without need to re-enforce the weakened wall.

16 Claims, 3 Drawing Sheets

MULTI-LUMEN CATHETER

BACKGROUND OF THE INVENTION

1. Technical Field

This invention relates to a multi-lumen catheter. More particularly, the invention relates to a triple lumen catheter having two relatively large central channels, plus a smaller channel in the outer peripheral wall.

2. State of the Art

Physicians use feeding-decompression catheters (gastrointestinal catheters) to feed distally and aspirate proximally. They have the feeding and aspiration (suction) sites separated by more than three inches to prevent unwanted removal of some or all of the feedings. Feeding-decompression catheters must be able to reside within the gastrointestinal (G-I) tract of patients for prolonged periods.

Some catheters are single lumen catheters and others are dual lumen devices which include feeding and aspirating tubes. Such single and dual lumen catheters are disclosed in U.S. Pat. Nos. 3,618,613; 4,543,089; 4,642,092; 4,705,511; 4,806,182; 5,334,169; 5,520,662; 5,599,325; 5,676,659; 5,807,311; 5,947,940; 6,447,472; 6,508,804; 6,659,974; 6,881,211; 6,921,396; 6,949,092; 7,048,727; and 8,409,169, the contents of which are incorporated entirely herein by reference.

When adding a third channel (lumen), for example to inflate a balloon, the wall must be reinforced on the interior of the catheter to prevent kinking at the weakened site. Kinks at the point of the third channel result in the catheter forming a teardrop shape, occluding or making use as an inflation channel or contrast radiography channel difficult.

The need to add plastic for re-enforcement encroaches on the useful intra-luminal area. Accordingly, what is needed is a triple lumen gastrointestinal catheter which avoids kinking, without the need for re-enforcement at the site of weakening to provide the third channel.

DISCLOSURE OF THE INVENTION

The disclosed invention relates to a gastrointestinal catheter comprising a catheter main body, wherein the catheter main body comprises an outer peripheral wall and an internal partition (septum) intersecting the outer peripheral wall to form a first and second lumen extending along a longitudinal axis defined by the catheter main body; and a third lumen disposed within the outer peripheral wall, at the intersection of the outer peripheral wall and the internal partition.

The disclosed invention further relates to a method of using a gastrointestinal catheter, the method comprising placing a gastrointestinal catheter in a patient, wherein the catheter comprises an outer peripheral wall and an internal partition intersecting the outer peripheral wall, the intersection of the internal partition and the outer peripheral wall forming a first lumen and a second lumen; and a third lumen disposed within the outer peripheral wall, at the intersection of the outer peripheral wall and the internal partition.

The foregoing and other features and advantages of the invention will be apparent to those of ordinary skill in the art from the following more particular description of the invention and the accompanying drawings.

DETAILED DESCRIPTION OF EMBODIMENTS OF THE INVENTION

Figure 1:
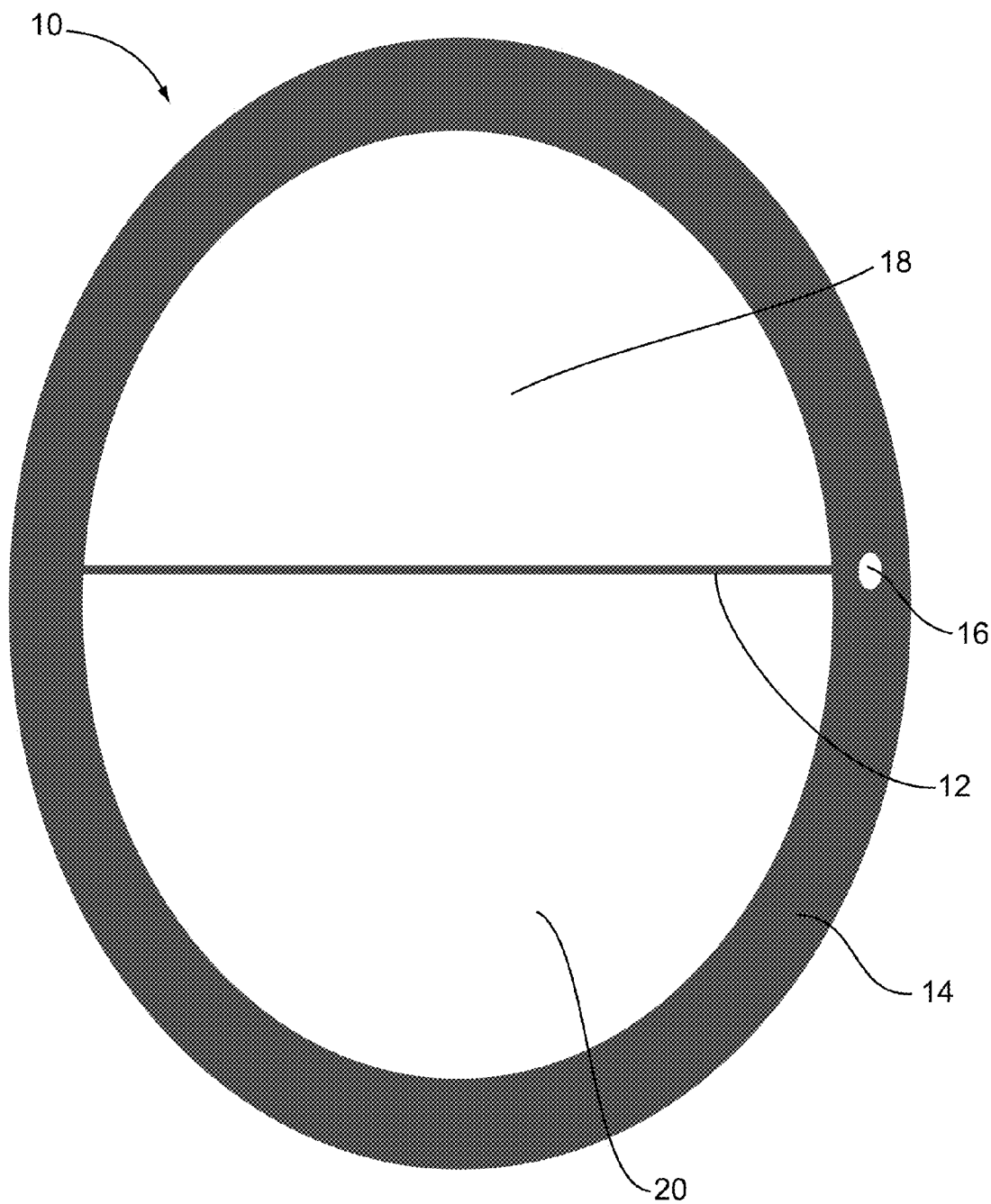
FIG. 1 shows a cross sectional view of a triple lumen gastrointestinal catheter in accordance with the invention.

As discussed above, embodiments of the present invention relate to a gastrointestinal catheter having a feeding and aspiration channel.

A catheter may be delivered by direct penetration through the abdominal and gastric or intestinal walls. Some directly placed catheters may then be directed to traverse the normal G-I channels to reach a more distal duodenal or jejunal feeding and/or aspiration site.

Alternatively, the catheter may be introduced indirectly and less traumatically into the body through a natural opening (e.g., nasal passage), to then traverse the natural G-I channels to the gastric or intestinal feeding and/or aspiration site.

Medical catheters are made of biocompatible elastomers, such as polyurethane. For example, in a single lumen polyurethane catheter, there is a minimum wall thickness that will withstand the expected forces that otherwise might result in kinking. Therefore, the walls are relatively thick to prevent kinking. However, they are manufactured as thin as can be tolerated without kinking under the conditions of use. Dual channel catheters are required for some applications. A single channel catheter design can be modified by forming a very thin internal partition (septum) between opposite walls during manufacture. For patient safety, fluid is delivered under very low pressure, i.e., gravity, so this partition can be made quite thin, relative to the encircling wall.

Triple lumen catheters are also required for some applications where a third channel is needed whose lumen diameter may be smaller. The triple lumen catheter may, when compressed during use, form a teardrop type shape, occluding the smaller channel. Generally, extruding a small diameter channel within the exterior wall introduces a potential point weakness. It would become vulnerable to kinking at this point. Adding another lumen within the catheter's wall introduces a potential point of weakness that may lead to a teardrop shape, with the kinking at the lumen within the wall.

Generally, when adding a third lumen, it is necessary to reinforce the weakened wall at the site of the third channel. However, in the gastrointestinal catheter of the present invention, no reinforcement is needed at the smallest channel site.

In the present invention, a gastrointestinal catheter having a first feeding channel, a second aspiration channel, and a third balloon inflation channel is disclosed. The third smallest channel can be extruded within the outer peripheral (exterior) wall of the catheter tube. The weakening and vulnerability of the outer peripheral wall to kinking at the third channel site is offset by the elastic pull of a flexible partition or membrane. There is no need to re-enforce the outer-peripheral wall to prevent kinking.

In the gastrointestinal catheter of the present invention, a third channel, for example a balloon inflation channel, may be extruded within the encircling outer peripheral wall without increasing the catheter's vulnerability to kinking. This requires positioning the channel at the junction of the outer peripheral wall and the origin of the thin flexible internal partition. Similar to the third channel, a fourth smaller channel, for example, a contrast radiography channel, may be added and positioned at the other junction of the outer peripheral wall and the origin of the thin flexible internal partition.

In the present invention, the feeding and suction channels of the gastrointestinal catheter are divided by a flexible internal partition (septum). The internal partition intersecting the exterior wall extends along a longitudinal axis defined by the catheter. The exterior wall of the gastrointestinal catheter may be circular. The exterior outer peripheral wall may also be oval if the flexible partition is deliberately shortened. This may be required for a balloon inflation channel that is larger than can be compensated for by simple elastic recoil of the internal partition. The weakening and vulnerability of the exterior wall to kinking at the inflation channel site can be offset by the elastic pull of the flexible partition.

The catheter of the present invention is resistant to kinking. The elastic recoil of the stretched internal partition provides a counter-force to prevent the kinking. By positioning the third and/or fourth lumen in the outer wall at (or near) the intersection of that wall with the internal partition, the potential forces resisting kinking offset any increased vulnerability to kinking introduced by adding that lumen. Adding the internal partition (septum) does not increase the catheter's vulnerability to kinking.

Figure 2:
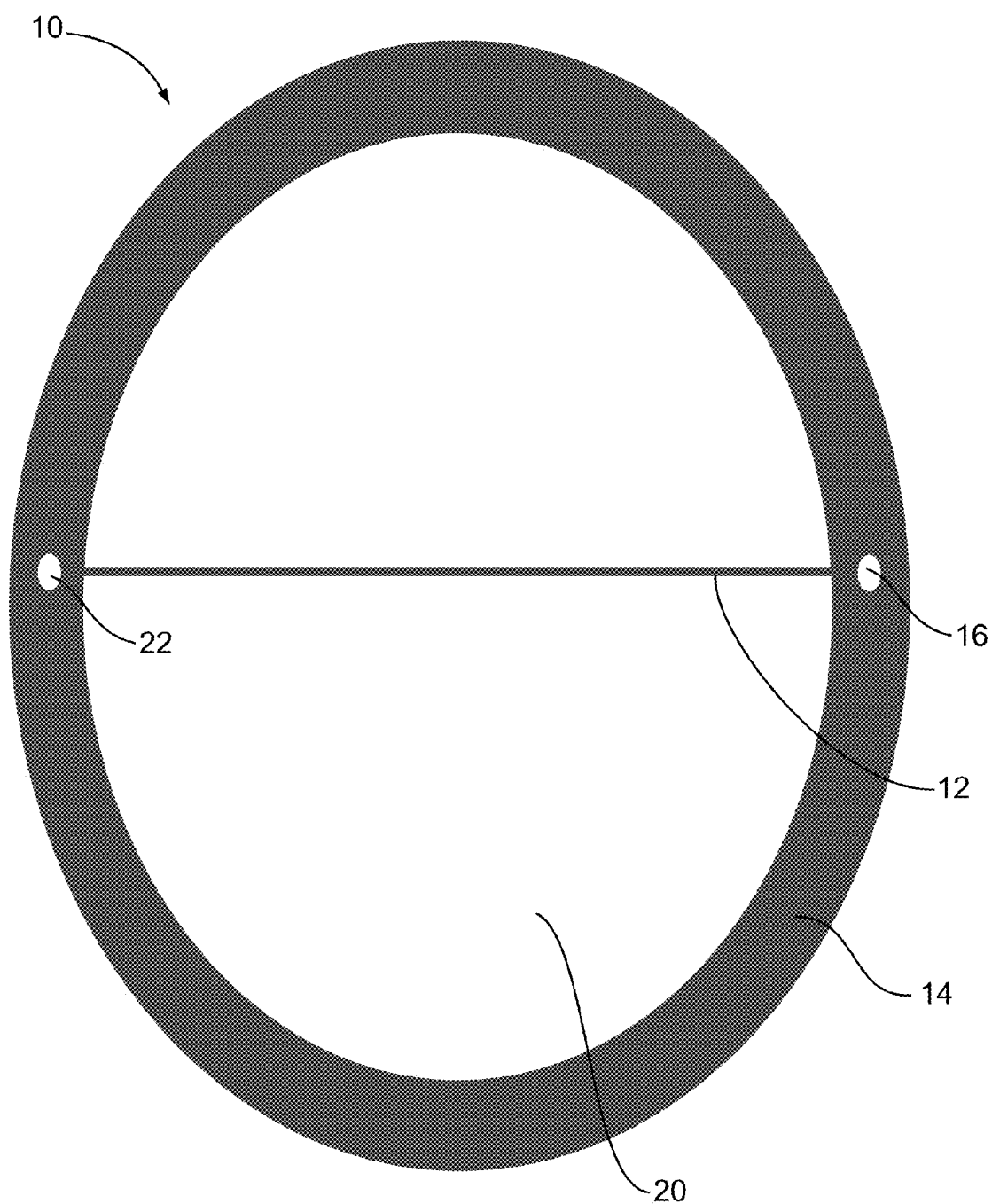
FIG. 2 shows a cross sectional view of a multi-lumen gastrointestinal catheter in accordance with the invention.

As shown in FIGS. 1 and 2 a multi-lumen catheter main body 10 is formed of a long flexible tube. FIG. 1 and FIG. 2 show a cross-section of catheter main body 10. A flexible internal partition wall 12 intersects outer peripheral wall 14. The flexible internal partition wall 12 extends the length of the catheter main body 10. The catheter main body 10 is formed of an elastomeric material, such as a polyurethane resin. The catheter main body 10 is in the form of a tube having a cylindrical (circular or oval) outer peripheral wall 14 with a substantially diametrically extending flexible internal partition wall 12 to divide the main body 10 internally into two equal channels or lumens, a first feeding channel 18 and a second aspiration channel 20, within the outer peripheral wall 14. Where the outer peripheral wall 14 and the flexible internal partition wall 12 intersect, a third smaller channel 16, which may be used as a balloon inflation channel, is provided. FIG. 2 shows a fourth smaller channel 22, which may be used for example, for contrast radiography.

Figure 3:
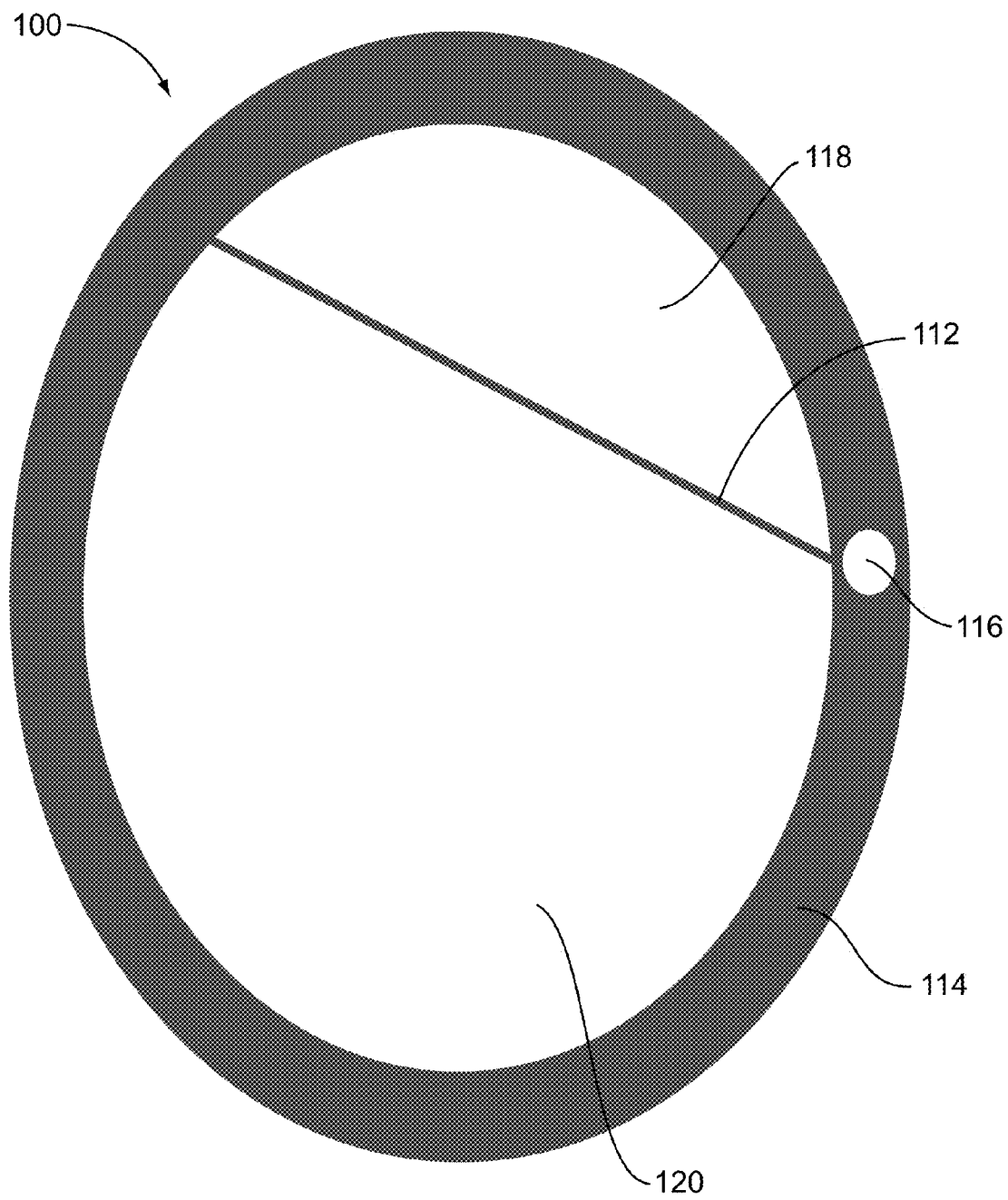
FIG. 3 shows a cross sectional view of a triple lumen gastrointestinal catheter in accordance with the invention.

As shown in FIG. 3, a multi-lumen catheter main body 100 is formed of a long flexible tube. A flexible internal partition wall 112 intersects outer peripheral wall 114. The flexible partition wall 112 extends the length of the catheter main body 100. The catheter main body 100 is formed of an elastomeric material, such as a polyurethane resin. The catheter main body 100 is in the form of a tube having a cylindrical (circular or oval) outer peripheral wall 114 with a flexible internal partition wall 112 extending across main body 100 to divide the main body 100 internally into two channels or lumens, having a smaller feeding channel 118 and a larger aspiration channel 120, within the outer peripheral wall 114. Where the outer peripheral wall 114 and the flexible internal partition wall 112 intersect, a smaller third channel 116, which may be used as a balloon inflation channel, is provided.

Generally, the aspiration channel: feeding channel area ratio is in the range of about 1:3 to about 3:1, particularly an aspiration channel: feeding channel area ratio of about 3:1.

Generally, the outer diameter (O.D.) of the catheter tube is in the range of from about 4.0 to about 6.5 mm, more generally about 5.5 to about 6.5 mm, particularly about 6.0 mm. Generally, the inner diameter (I.D.) of the catheter tube is in the range of from about 2.75 to about 4.00 mm, more generally in the range of about 3.00 to about 4.00 mm, particularly about 3.50 mm.

Generally, the outer peripheral wall thickness is in the range of from about 0.75 to about 1.75 mm, more generally about 1.00 to about 1.50 mm, particularly about 1.25 mm.

Generally, the internal partition wall thickness is in the range of from about 0.10 to about 0.50 mm, particularly about 0.25 mm.

Generally, the I.D. of the third and/or fourth smaller channels is in the range from about 0.05 to about 0.10 mm, particularly about 0.05 mm. The third and/or fourth channel can be enlarged, if desired, still without need to re-enforce. The catheter tube can be deformed from round to oval by shortening the length of the partition by about 10%. Therefore, the catheter would be extruded with a slightly shorter flexible internal partition. The ratio of the I.D. of the catheter tube: length of the internal partition is about 90%, which would result in the catheter having a slight initial oval shape. The kinking of the catheter would continue to be resisted by the increased elastic recoil of the encircling wall, as determined by Young's Elastic Modulus for the polymer.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above.

What is claimed is:

1. A gastrointestinal catheter comprising:
   a catheter main body, wherein the catheter main body comprises
      an outer peripheral wall having a continuous internal surface and a constant thickness;
      an internal partition intersecting the outer peripheral wall to form a first and second lumen extending along a longitudinal axis defined by the catheter main body; and
      a third lumen disposed within the outer peripheral wall, at the intersection of the outer peripheral wall and the internal partition.

2. The gastrointestinal catheter of claim 1, wherein the first and second lumens are of equal size.

3. The gastrointestinal catheter of claim 1, wherein the third lumen has a smaller cross-sectional area than the first and second lumens.

4. The gastrointestinal catheter of claim 1, wherein a fourth lumen is disposed within the outer peripheral wall, at the intersection of the outer peripheral wall and the internal partition.

5. The gastrointestinal catheter of claim 1, wherein the catheter main body is polyurethane.

6. The gastrointestinal catheter of claim 1, wherein the outer peripheral wall thickness is in the range of from about 0.75 to about 1.75 mm.

7. The gastrointestinal catheter of claim 1, wherein the I.D. of the third lumen is in the range from about 0.05 to about 0.10 mm.

8. The gastrointestinal catheter of claim 1, wherein the internal partition is flexible.

9. The gastrointestinal catheter of claim 1, wherein the first lumen is a feeding channel.

10. The gastrointestinal catheter of claim 1, wherein the second lumen is an aspiration channel.

11. A method of using a gastrointestinal catheter, the method comprising:
    placing a gastrointestinal catheter in a patient, wherein the catheter comprises an outer peripheral wall having a continuous internal surface and a constant thickness and an internal partition intersecting the outer peripheral wall, the intersection of the internal partition and the outer peripheral wall forming a first lumen and a second lumen; and a third lumen disposed within the outer peripheral wall, at the intersection of the outer peripheral wall and the internal partition.

12. The catheter of claim 11, wherein the first and second lumens are of equal size.

13. The method of claim 11, wherein a fourth lumen is disposed within the outer peripheral wall, at the intersection of the outer peripheral wall and the internal partition.

14. The method of claim 11, wherein the catheter main body is polyurethane.

15. The method of claim 11, wherein the third lumen is a balloon inflation channel.

16. The method of claim 13, wherein the fourth lumen is for contrast radiography.

* * * * *